(12) United States Patent
Brahm

(10) Patent No.: US 10,568,914 B1
(45) Date of Patent: Feb. 25, 2020

(54) HUMAN BIRTH TISSUE LAMINATE AND METHODS OF USE

(71) Applicant: BioDLogics, LLC, Cordova, TN (US)

(72) Inventor: Timothy R. Brahm, Germantown, TN (US)

(73) Assignee: BioDLogics, LLC, Cordova, TN (US)

( * ) Notice: Subject to any disclaimer, the term of this patent is extended or adjusted under 35 U.S.C. 154(b) by 49 days.

(21) Appl. No.: 15/823,743

(22) Filed: Nov. 28, 2017

Related U.S. Application Data

(62) Division of application No. 14/202,360, filed on Mar. 10, 2014, now Pat. No. 9,855,301.

(60) Provisional application No. 61/778,557, filed on Mar. 13, 2013.

(51) Int. Cl.
*A61K 35/51* (2015.01)
*A61K 35/50* (2015.01)

(52) U.S. Cl.
CPC .............. *A61K 35/51* (2013.01); *A61K 35/50* (2013.01)

(58) Field of Classification Search
None
See application file for complete search history.

(56) References Cited

U.S. PATENT DOCUMENTS

| | | | |
|---|---|---|---|
| 4,120,649 A | 10/1978 | Schechter | |
| 4,361,552 A | 11/1982 | Baur, Jr. | |
| 4,674,488 A | 6/1987 | Campbell | |
| 4,894,063 A | 1/1990 | Nashef | |
| 5,607,590 A | 3/1997 | Shimizu | |
| 5,618,312 A | 4/1997 | Yui | |
| 6,152,142 A | 11/2000 | Tseng | |
| 6,254,637 B1 | 7/2001 | Lee | |
| 6,326,019 B1 | 12/2001 | Tseng | |
| 8,105,634 B2 | 1/2012 | Liu | |
| 8,932,805 B1 | 1/2015 | Brahm | |
| 2001/0053839 A1 | 12/2001 | Noishiki | |
| 2003/0187515 A1 | 10/2003 | Hariri | |
| 2003/0225355 A1 | 12/2003 | Butler | |
| 2004/0048796 A1 | 3/2004 | Hariri | |
| 2007/0021704 A1* | 1/2007 | Hariri | A61F 13/069 602/48 |
| 2007/0031471 A1 | 2/2007 | Peyman | |
| 2007/0038298 A1 | 2/2007 | Sulner | |
| 2008/0044848 A1 | 2/2008 | Heidaran | |
| 2008/0046095 A1 | 2/2008 | Daniel | |
| 2008/0131522 A1 | 6/2008 | Liu | |
| 2008/0193554 A1 | 8/2008 | Dua | |
| 2008/0274184 A1 | 11/2008 | Hunt | |
| 2009/0208551 A1 | 8/2009 | Jung | |
| 2010/0104539 A1 | 4/2010 | Daniel | |
| 2010/0106233 A1 | 4/2010 | Deeken | |
| 2011/0129520 A1 | 6/2011 | Blood | |
| 2011/0189301 A1 | 8/2011 | Chun | |
| 2012/0009644 A1 | 1/2012 | Goldstein | |
| 2012/0009679 A1 | 1/2012 | Walsh | |
| 2012/0078378 A1 | 3/2012 | Spencer | |
| 2012/0083900 A1 | 4/2012 | Wilkins | |
| 2014/0052274 A1 | 2/2014 | Koob | |

FOREIGN PATENT DOCUMENTS

| | | |
|---|---|---|
| CN | 1799558 | 7/2006 |
| EP | 0781564 A2 | 7/1997 |
| WO | 2009044408 A1 | 4/2009 |
| WO | 2012003377 A2 | 1/2012 |
| WO | 2012112417 A2 | 8/2012 |
| WO | 2012112441 A1 | 8/2012 |
| WO | 2013032938 A1 | 3/2013 |

* cited by examiner

*Primary Examiner* — Michelle F. Paguio Frising
(74) *Attorney, Agent, or Firm* — Barnes & Thornburg LLP

(57) ABSTRACT

A laminated graft fabricated from human birth tissue material comprising at least two amniotic membranes, or at least two chorionic membranes, or at least one amniotic membrane and at least one chorionic membrane, and at least one morselized placental composition to form a human birth tissue laminate graft. Methods of processing human birth tissue material to form a laminated graft are also provided. Additionally, methods for treating a wound or defect and methods of promoting regeneration of diseased or damaged tissue are provided.

18 Claims, 4 Drawing Sheets

HUMAN BIRTH TISSUE LAMINATE AND METHODS OF USE

CROSS-REFERENCE TO RELATED APPLICATIONS

This application claims priority to U.S. application Ser. No. 14/202,360 filed Mar. 10, 2014 which claims priority to U.S. Provisional Patent Application No. 61/778,557 filed Mar. 13, 2013, the contents of which are each incorporated herein in their entirety.

FIELD OF THE INVENTION

The present invention is directed to a human birth tissue laminate composed of aseptically recovered human birth tissue, as well as methods of processing the same to prepare a human birth tissue laminate and methods of using the same.

BACKGROUND OF THE INVENTION

Human placental tissue has been used in various surgical procedures, including skin transplantation and ocular surface disorders, for over a century. The tissue has been shown to provide good wound protection, prevent surgical adhesions, reduce pain, reduce wound dehydration, and provide anti-inflammatory and anti-microbial effects.

The placenta is a fetomaternal organ consisting of a placental globe, umbilical cord, associated membranes (chorionic membrane and amniotic membrane), Wharton's jelly, amniotic fluid and other placental gelatins, fluids, cells and extracellular material. The chorionic membrane and the amniotic membrane are attached by loose connective tissue and make up the placental sac. The innermost membrane of the placental sac is the amniotic membrane, which comes into contact with the amniotic fluid that surrounds the fetus. The amniotic membrane is avascular and lined by simple columnar epithelium overlying a basal membrane. The chorionic membrane is the outermost layer of the sac and is heavily cellularized. The placental membranes have an abundant source of collagen that provides an extracellular matrix to act as a natural scaffold for cellular attachment in the body. Collagen provides a structural tissue matrix that facilitates, among other things, cell migration and proliferation in vivo.

Various manufacturing processes have also been employed to create wound coverings composed of amniotic membrane, chorionic membrane, or intact amniotic and chorionic membranes recovered aseptically from human birth tissue after elective Cesarean surgery. There remains a need, however, for human birth tissue grafts that are uniquely processed to enhance the tissue's physical properties and to provide a material that can be stored for easy use.

SUMMARY OF THE INVENTION

The present invention is generally directed to a human birth tissue laminate and processes for producing the human birth tissue laminate. The human birth tissue laminate of the present invention is a sterile, biocompatible structure placed on or around a wound or defect that aids in the healing cascade by reducing or preventing clot formation, preventing fibrous scar formation, and reducing pain and inflammation after implantation. In some aspects, the human birth tissue laminate may be used in guide tissue regeneration techniques, e.g., to regenerate or replace diseased or damaged tissue, including soft tissue and bone.

According to one embodiment, a human birth tissue laminate is provided that includes at least two amniotic membranes, or at least two chorionic membranes, or at least one amniotic membrane and at least one chorionic membrane, and at least one morselized placental composition, to form a human birth tissue laminate graft. The morselized placental composition can include all or portions of the placental globe, umbilical cord, umbilical cord blood, umbilical cord vessel(s), amniotic membrane, chorionic membrane, Wharton's jelly, amniotic fluid, or any combination thereof. According to one aspect, the amniotic membrane(s) and/or chorionic membrane(s) of the human birth tissue laminate are cross-linked using a cross-linking solution. In one embodiment, the cross-linking solution comprises from about 0.05% to about 3% glutaraldehyde. According to another aspect of the present invention, the membrane(s) is/are treated with at least one alcohol composition, which may comprise an ethanol composition. According to a preferred embodiment, the ethanol composition comprises from about 90% to about 100% ethanol. The human birth tissue laminate may be terminally sterilized using gamma irradiation or electron beam irradiation.

According to another aspect, a method of preparing a membrane for a human birth tissue laminate is provided. The method includes the steps of:

(a) obtaining amniotic membrane, chorionic membrane, or both amniotic and chorionic membrane from a seronegative, healthy human via Cesarean section or vaginal delivery;

(b) temporarily storing the membrane in a sterile saline solution;

(c) rinsing the membrane with a sterile saline solution;

(d) covering the membrane with a substrate on both the fetal membrane side and the maternal membrane side;

(e) optionally, immersing the membrane in a preservative solution for a period of up to about 20 minutes, wherein the preservative solution comprises from about 0.05% to about 3% glutaraldehyde, an alcohol composition or a combination thereof;

(f) optionally, rinsing the membrane with a sterile saline solution;

(g) optionally, soaking the membrane in a sterile saline solution;

(h) optionally, immersing the membrane in an alcohol composition; and (i) cutting the membrane to a predetermined size to form a membrane for a human birth tissue laminate.

The method of preparing a membrane for a human birth tissue laminate may further include the step of removing the chorionic membrane via blunt dissection and discarding the chorionic membrane in step (a). According to one embodiment, the sterile saline solution in step (b), step (c), step (f) and step (g) comprises from about 0.9% to about 20% NaCl. In a preferred embodiment, the sterile saline solution in step (b) comprises 18% NaCl. In a preferred embodiment, the sterile saline solution in step (c) comprises 0.9% NaCl. According to one aspect, the preservative solution in step (e) comprises 0.1% glutaraldehyde. According to another aspect, the alcohol composition in steps (e) and (h) comprises an ethanol composition. In one embodiment, the ethanol composition comprises from about 90% to about 100% ethanol. In a preferred embodiment, the alcohol composition in steps (e) and (h) comprises 95.5% ethanol. In another preferred embodiment, the alcohol composition in steps (e) and (h) comprises 100% ethanol.

According to another aspect, a method of preparing a morselized placental composition for a human birth tissue laminate is provided. The method includes the steps of:

(a) obtaining human birth tissue material from a seronegative, healthy human via Cesarean section or vaginal delivery;

(b) temporarily storing the human birth tissue material in a sterile saline solution;

(c) cutting the human birth tissue material;

(d) removing residual blood and sterile saline solution from the human birth tissue material;

(e) rinsing the human birth tissue material with a sterile saline solution;

(f) soaking the human birth tissue material in a sterile saline solution; and (g) subjecting the human birth tissue material to morselization to form a morselized placental composition.

The method of preparing a morselized placental composition for a human birth tissue laminate may further comprise any one or all of the following steps after step (f) and before step (g):

(i) removing residual blood and sterile saline solution from the human birth tissue material;

(ii) rinsing the human birth tissue material with a sterile saline solution;

(iii) soaking the human birth tissue material in a sterile saline solution; and/or (iv) removing residual blood and sterile saline solution from the human birth tissue material.

The aforementioned steps (i)-(iv) may be performed at least two times. In another aspect, the aforementioned step (e) is repeated four times. In another aspect, the aforementioned step (i) is repeated three times. According to another embodiment, the sterile saline solution comprises from about 0.9% to about 20% NaCl. According to one aspect, the human birth tissue material used to prepare a morselized placental composition may include the placental globe, umbilical cord, umbilical cord blood, umbilical cord vessel(s), amniotic membrane, chorionic membrane, Wharton's jelly, amniotic fluid, or any combination thereof.

The method of preparing a morselized placental composition for a human birth tissue laminate may further include the steps of:

(g) soaking the morselized placental composition in an ethanol composition; and (h) drying the morselized placental composition.

In one embodiment, the ethanol composition is 100% ethanol.

According to another aspect, a method of preparing a human birth tissue laminate is provided. The method includes the steps of:

providing a first membrane;

providing a second membrane;

providing a pre-determined amount of a morselized placental composition;

placing the morselized placental composition on an interior face of the first membrane; and securing the second membrane over the morselized placental composition and onto the interior face of the first membrane to form a human birth tissue laminate.

In one embodiment, the first and second membranes are independently selected from the group consisting of at least one amniotic membrane, at least one chorionic membrane, and a combination thereof. In one embodiment, the step of securing the second membrane to the first membrane is accomplished by applying an adhesive to either or both the first or second membrane. In another embodiment, the step of securing the second membrane to the first membrane is accomplished by vacuum lamination. In one embodiment, the interior face of the first membrane corresponds to the fetal side of the first membrane. In another embodiment, a maternal side of the second membrane is secured to the interior face of the first membrane.

According to another aspect, a human birth tissue laminate is provided that is produced by the aforementioned method. According to another aspect, the method for producing a human birth tissue laminate can further include packaging the human birth tissue laminate graft in a dry state or a wet state; and terminally sterilizing the packaged human birth tissue laminate graft using irradiation.

According to another aspect, a method of treating a wound or defect is provided. The method includes the steps of preparing a human birth tissue laminate graft according to methods provided herein and placing the human birth tissue laminate graft on or around the wound or defect. The wound can include be a diabetic ulcer, decubitus ulcer, venous leg ulcer, arterial leg ulcer, cutaneous ulcer, or a wound arising on or around a soft tissue, nerve, organ, vascular tissue, muscle, spinal cord, bone, oral cavity, ocular surface, or a combination thereof. According to one embodiment, the defect is a soft tissue defect or bone void. According to one embodiment, the method of treating a wound or defect can further comprise the step of hydrating the human birth tissue laminate graft prior to application.

According to another aspect, a method of promoting regeneration of diseased or damaged tissue is provided. The method includes the steps of preparing a human birth tissue laminate according to the methods provided herein; and placing the human birth tissue laminate graft on or around the diseased or damaged tissue. According to one embodiment, the tissue is soft tissue, nerve, organ, vascular tissue, muscle, spinal cord, bone, oral cavity, ocular surface, or a combination thereof. According to one embodiment, the method of promoting regeneration of diseased or damaged tissue can further comprise the step of hydrating the human birth tissue laminate graft prior to application.

According to another aspect, a kit for use by a medical professional is provided. The kit includes one or more packaged and sterilized human birth tissue laminates as provided herein. The kit may further include at least one set of instructions.

DETAILED DESCRIPTION OF THE INVENTION

Figure 1:
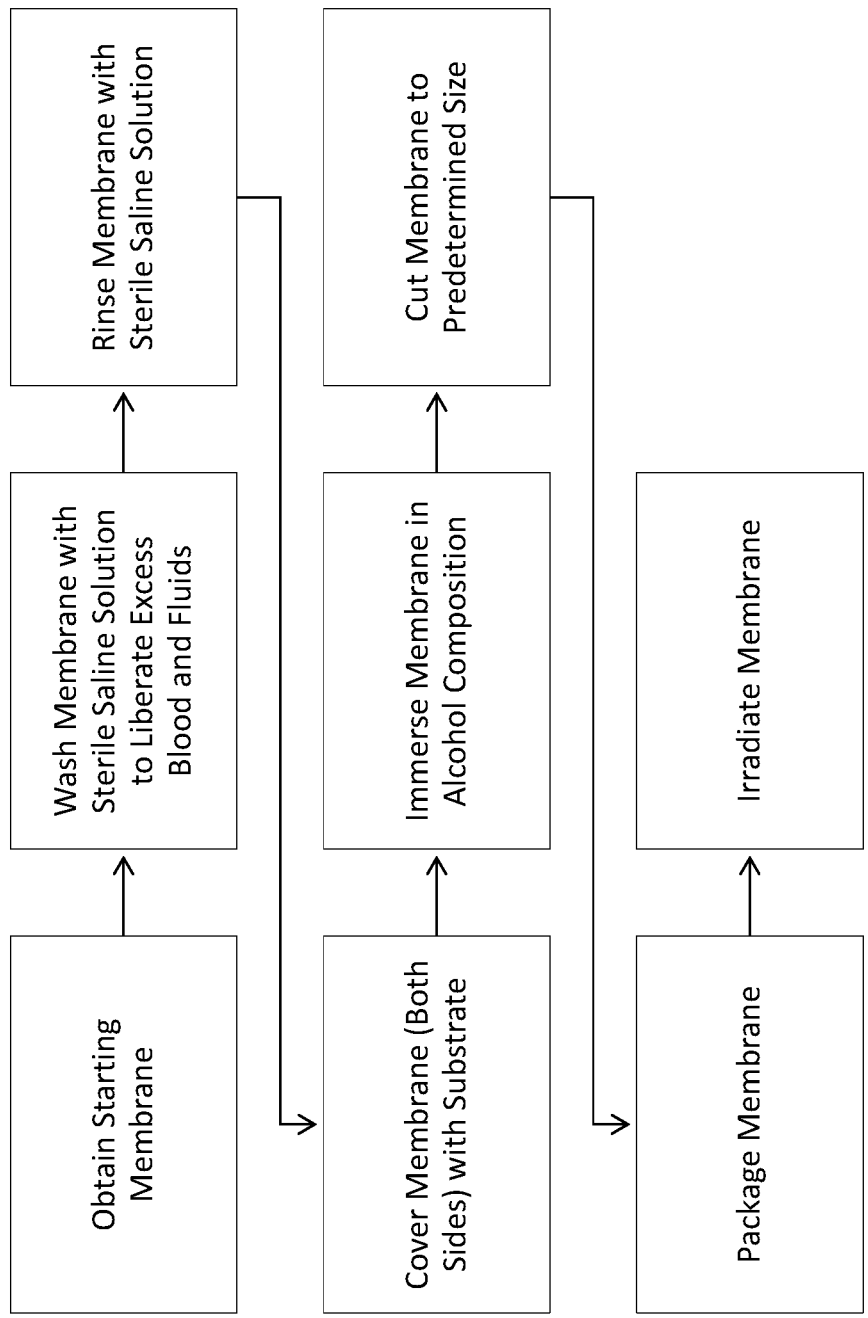
FIG. 1 illustrates a method of preparing a membrane for a human birth tissue laminate.

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the present disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise. As used in the specification, and in the appended claims, the words "optional" or "optionally" mean that the subsequently described event or circumstance can or cannot occur. For example, the phrase "optionally soaking the membrane" means that the soaking step may or may not be performed.

As used herein, the term "human birth tissue" includes, but is not limited to, elements of the placental organ such as, for example, placental globe, umbilical cord, umbilical cord vessels, umbilical cord blood, chorionic membrane, amniotic membrane, Wharton's jelly, amniotic fluid and other placental gelatins, fluids, cells and extracellular material obtained from a seronegative, healthy female.

The present invention generally relates to the use of at least two amniotic membranes; or at least two chorionic membranes; or at least one amniotic membrane and at least one chorionic membrane; and at least one morselized placental composition to form a human birth tissue laminate graft. In a preferred embodiment, the human birth tissue laminate graft is a sterile, biocompatible structure that aids in the healing cascade by reducing or preventing clot formation, preventing fibrous scar formation, and reducing pain and inflammation after implantation. In another preferred embodiment, the human birth tissue laminate may be used in guided tissue regeneration techniques, e.g., to regenerate or replace diseased or damaged tissue, including soft tissue and bone.

The human birth tissue components giving rise to the human birth tissue laminate graft of the present invention provides handling characteristics useful for placement and implantation. In one embodiment, the human birth tissue laminate graft is flexible and readily conforms to multiplanar shapes (e.g., can conform to the geometry of the wound, defect or application site). In certain embodiments, the human birth tissue laminate graft is fully resorbed by the body after placement. In other embodiments, the human birth tissue laminate graft remains intact on or around a wound, defect or application site.

In certain embodiments, the human birth tissue laminate graft may be of various physical sizes, thicknesses, and shapes. According to such an embodiment, the human birth tissue laminate graft is preferably of sufficient size and shape to be applied onto or around a wound or defect. The human birth tissue laminate graft thickness may vary depending on the membrane composition(s), the number of membrane layers, and the intended use. In certain embodiments, the human birth tissue laminate readily conforms to the geometry of an application site. The size of the human birth tissue laminate graft may be adjusted to a desired size and shape at the time of implantation by a medical professional using any method known in the art (e.g., trimming and suturing).

To obtain the human birth tissue material needed to prepare a human birth tissue laminate, potential human birth tissue donors providing informed consent are pre-screened during an examination of pre-natal medical records and blood test results. A comprehensive medical history and behavior risk assessment is obtained from the donor prior to donation incorporating U.S. Public Health Service guidelines. Discussions with the physician(s) and/or the donor mother are conducted to identify circumstances that may lead to the exclusion of the donor or donated tissue. Additionally, a physical exam is performed on the donor to determine whether there is evidence of high risk behavior or infection and to determine the overall general health of the donor.

Infectious disease testing of donor blood specimens is performed for each tissue donor on a specimen collected at the time of donation or within seven days prior to or after donation. Exemplary infectious disease testing includes, but is not limited to, antibodies to the human immunodeficiency virus, type 1 and type 2 (anti-HIV-1 and anti-HIV-2); nucleic acid test (NAT) for HIV-1; hepatitis B surface antigen (HBsAg); total antibodies to hepatitis B core antigen (anti-HBc—total, meaning IgG and IgM); antibodies to the hepatitis C virus (anti-HCV); NAT for HCV; antibodies to human T-lymphotropic virus type I and type II (anti-HTLV-I and anti-HTLV-II); and syphilis (a non-treponemal or treponemal-specific assay may be performed).

Human birth tissue is preferably recovered from a full-term aseptic Cesarean delivery of a newborn. Alternatively, human birth tissue is recovered from a full-term vaginal delivery of a newborn. The placental globe, umbilical cord, umbilical cord vessels, umbilical cord blood, chorionic membrane, amniotic membrane, Wharton's jelly, amniotic fluid and other placental gelatins, fluids, cells and extracellular material can be recovered from a seronegative, healthy female after the newborn is removed. In particular embodiments where only the amniotic membrane and the placental globe are selected for further processing, portions of the human birth tissue material (e.g., chorionic membrane or umbilical cord) may be removed and discarded by blunt dissection or excision. For example, the chorionic membrane may be removed by applying finger pressure and sliding it off of the amniotic membrane using as little pressure as possible to avoid tearing of the amnion.

The birth tissue material may be initially rinsed with a sterile saline solution to remove any blood or debris. According to one embodiment, the sterile saline solution comprises from about 0.9% to about 20% NaCl. According to a preferred embodiment, the sterile saline solution comprises 18% NaCl. According to one embodiment, this rinse step may be repeated multiple times. In a preferred embodiment, the rinse step is repeated for a total of three times.

The birth tissue material may be initially stored in a sterile saline solution at a temperature between about 1° C. to about 10° C. for a period of up to about 120 hours prior to further processing. According to one embodiment, the sterile saline solution comprises from about 0.9% to about 20% NaCl. According to a preferred embodiment, the sterile saline solution comprises 15% NaCl. According to another preferred embodiment, the sterile saline solution comprises 18% NaCl.

Processing Amniotic Membrane, Chorionic Membrane or Amniotic and Chorionic Membrane According to a preferred embodiment, the human birth tissue laminate of the present invention encompasses two or more membrane components. These membrane components may include at least two amniotic membranes, or at least two chorionic membranes, or at least one amniotic membrane and at least one chorionic membrane. Thus, the term "membrane" as described herein includes amniotic membrane, chorionic membrane or amniotic and chorionic membrane.

The membranes giving rise to the human birth tissue laminate as described herein may be produced by processing human birth tissue according to the steps provided herein. Throughout processing, the orientation of a membrane (either fetal side or material side) may be identified and maintained to ensure appropriate orientation in the final human birth tissue laminate. Processing does not change the physical properties of the resulting membrane so as to yield the membrane tissue unacceptable for clinical use. Instruments, solutions, and supplies coming into contact with tissue during the processing of the membranes are sterile. All surfaces coming in contact with tissue intended for transplant are either sterile or draped using aseptic technique.

According to one embodiment, the membrane is immersed in a basin containing a sterile saline solution. According to one embodiment, the sterile saline solution includes typically from about 0.9% to about 20% NaCl. In a preferred embodiment, the sterile saline solution comprises 0.9% NaCl. Excess blood and fluids may be liberated from the membrane by gently stirring or swirling the fluid in a circular motion in the basin or by placing the basin on a shaker. The membrane can then be rinsed with a sterile saline solution. In one embodiment, the sterile saline solution includes NaCl in a concentration range of about 0.9% to about 20%. In a preferred embodiment, the sterile saline solution comprises 0.9% NaCl. The membrane may be rinsed in bowls or trays of sufficient size to allow the membrane to be spread out to improve the rinse coverage. Sufficient saline solution is utilized to ensure that the membrane is completely immersed. The saline is then decanted into a discard basin.

Multiple saline rinse cycles may be performed. In one embodiment, the membrane is rinsed for two or more separate rinse cycles, with each rinse cycle lasting for a maximum of five minutes. The membrane is covered with a substrate on both the fetal membrane side and the maternal membrane side. Appropriate substrates include, but are not limited to, a sterile mesh or polymer mesh of adequate size and shape for covering each side of the membrane.

According to a preferred embodiment, after the membrane is covered with an appropriate substrate, the membrane is sectioned into uniformly sized pieces (e.g., 4 cm×4 cm or 4 cm×8 cm). In certain embodiments, the membrane can be cut into particular shapes of any desired size by a rotary type cutting tool. A grooved or similarly indicated cutting board may be used to aid in cutting a straight and correctly sized membrane. In another embodiment, the membrane is cut by free hand using a scalpel and ruler to achieve the desired size.

Figure 2:
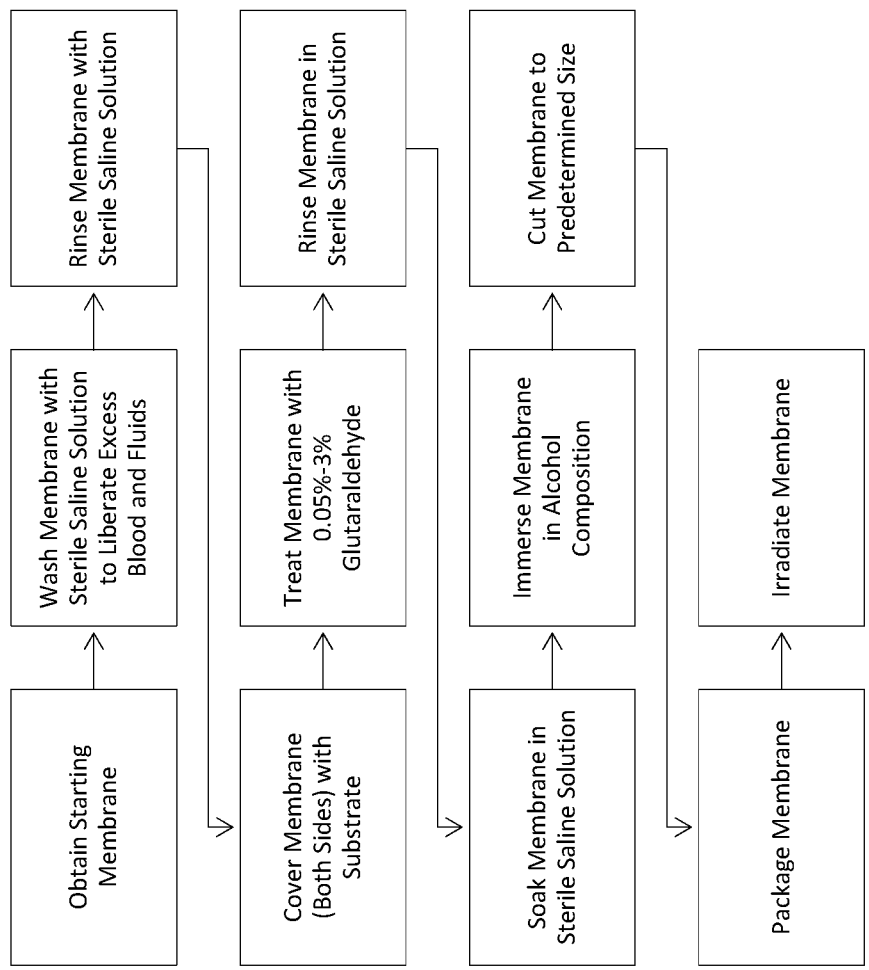
FIG. 2 illustrates a method of preparing a membrane for a human birth tissue laminate.

According to the embodiment as illustrated in FIG. 2, the membrane is then optionally immersed in a preservative solution for a period of time of typically up to about twenty minutes. The preservative solution includes typically from about 0.05% to about 3% glutaraldehyde and, preferably, about 0.1% glutaraldehyde. The membrane may then be optionally stirred or swirled at a temperature of typically about 22° C. (±1-5° C.). When present, glutaraldehyde leads to collagen cross-linking, which, in turn, leads to a significant increase in the biomechanical strength of the membrane. Additionally, the handling characteristics of the membrane are improved after glutaraldehyde treatment because the membrane is more rigid and does not fold over onto itself. Glutaraldehyde cross-linking also prohibits fast resorption of the membrane by the body after implantation. The glutaraldehyde treatment is preferably performed in a bowl or tray of sufficient size to allow the membrane to spread out in order to maximize exposure of the tissue to the glutaraldehyde solution. Sufficient glutaraldehyde solution should be used to immerse the membrane in the solution. Typically, a minimum of about 400 ml of glutaraldehyde solution is used.

Figure 3:
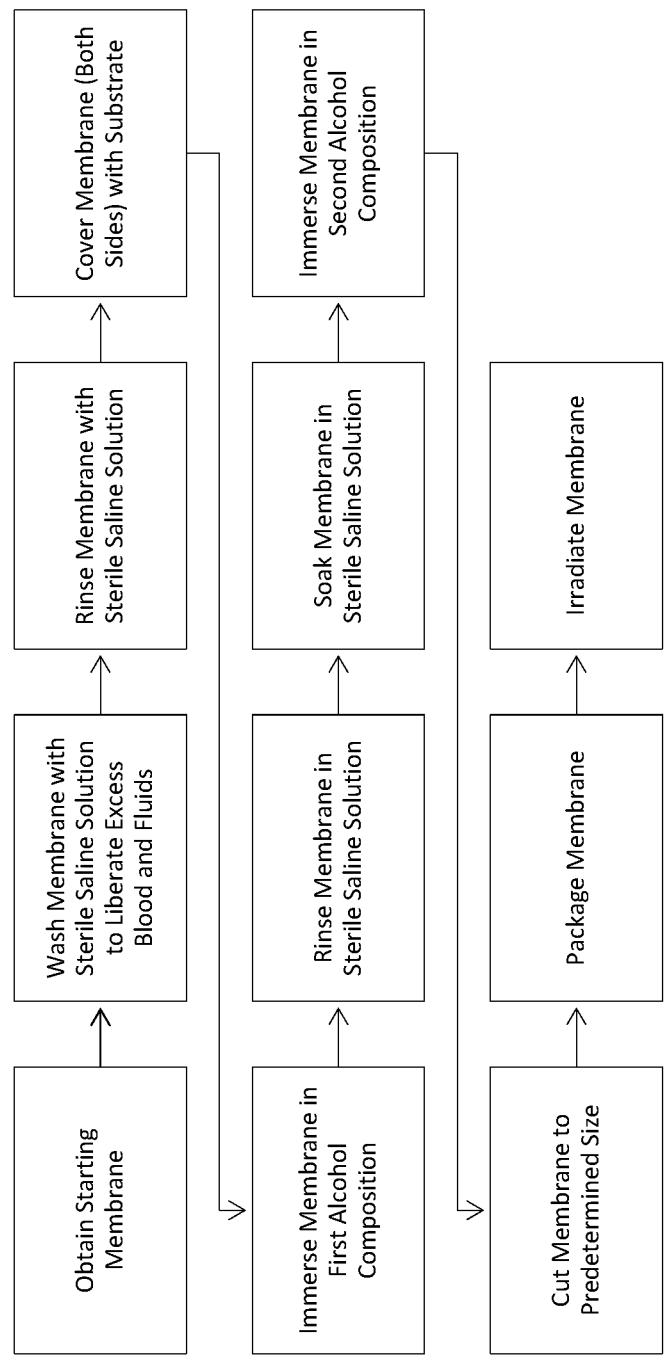
FIG. 3 illustrates a method of preparing a membrane for a human birth tissue laminate.

According to the alternative embodiment as illustrated in FIG. 3, the preservative solution may optionally include from about 90% to about 100% ethanol (i.e., in the absence of glutaraldehyde (see FIG. 3—referred to as "first alcohol composition")). In certain embodiments, the alcohol composition includes about 95.5% ethanol. In other embodiments, the alcohol composition includes about 100% ethanol. A membrane produced according to the embodiment of FIG. 3 will be resorbed more quickly by the body (as opposed to gluteraldehyde treatment followed by alcohol treatment).

As illustrated in the embodiments of FIG. 2 and FIG. 3, the membrane is then optionally rinsed with a sterile saline solution. Alternatively, the membrane is rinsed multiple times with a sterile saline solution. According to one embodiment, the sterile saline solution includes typically from about 0.9% to about 20% of NaCl. The membrane can then be optionally soaked in a sterile saline solution. According to one embodiment, the sterile saline solution includes typically from about 0.9% to about 20% of NaCl. According to one embodiment, soaking is conducted for a maximum period of about 35 minutes.

As illustrated in each of the embodiments of FIGS. 1, 2, and 3, the membrane is then immersed in an alcohol composition. The alcohol composition includes about 90% to about 100% ethanol. In certain embodiments, the alcohol composition includes about 95.5% ethanol. In other embodiments, the alcohol composition includes about 100% ethanol. Treatment of the membrane within a particular alcohol concentration range at this step in the process has yielded unexpected results related to the handling characteristics. One of ordinary skill in the art appreciates the difficulty of handling and manipulating amniotic and chorionic tissue during manipulation and application. Specifically, existing amniotic and chorionic grafts are difficult to place over or around a specific site, particularly because these grafts fold back over on themselves ("wrinkling"), rendering proper placement and positioning very challenging. When treated with the aforementioned alcohol composition, the resulting membrane experiences further cross-linking which aids in the handling characteristics of the membrane. The alcohol-treated membrane does not "wrinkle" and allows for ease of application to a specific site. Furthermore, the alcohol treatment is multi-functional, providing a means of sterilization, preservation, and chemical dehydration for the graft, in addition to serving as a radioprotectant for the construct prior to terminal irradiation.

As illustrated in each of the embodiments of FIGS. 1, 2, and 3, the membrane is then cut to the desired size. According to a preferred embodiment, the membrane is sectioned into uniformly sized pieces (e.g., 4 cm×4 cm or 4 cm×8 cm). In certain embodiments, the membrane can be cut into particular shapes of any desired size by a rotary type cutting tool. A grooved or similarly indicated cutting board may be used to aid in cutting a straight and correctly sized membrane. In another embodiment, the membrane is cut by free hand using a scalpel and ruler to achieve the desired size.

In alternate embodiments, the membrane may be prepared by any method commonly known in the art, including, but not limited to, air drying, chemical dehydration, lyophilization, vacuum oven dehydration, non-vacuum oven dehydration, incubator dehydration and cryopreservation.

Processing Morselized Placental Composition

The human birth tissue laminate of the present invention encompasses one or more morselized placental composition components. The morselized placental composition is prepared by the methods described herein. The one or more morselized placental composition components consists of human birth tissue material, including, but not limited to, placental globe, umbilical cord, umbilical cord blood, umbilical cord vessel(s), amniotic membrane, chorionic membrane, Wharton's jelly, amniotic fluid, or any combination thereof.

Instruments, solutions, and supplies coming into contact with tissue during the processing of the membranes are sterile. All surfaces coming in contact with tissue intended for transplant are either sterile or draped using aseptic technique. According to one aspect, the placental globe is separated from the chorion and the umbilical cord using blunt dissection and/or scalpel. The chorion and umbilical cord may be discarded after removal.

In a preferred embodiment, the morselized placental composition is composed of placental globe. The placental globe may be processed according to the steps provided herein. The placental globe may be cut into small pieces (non-uniform) using mayo scissors or the like. The resulting placental globe pieces may be placed in a handheld press or similar equipment, whereby residual blood and solution are pressed (e.g., removed) from the tissue. According to one embodiment, the placental globe pieces are rinsed with a sterile saline solution. According to one embodiment, the sterile saline solution comprises from about 0.9% to about 20% NaCl. According to a preferred embodiment, the sterile saline solution is 18%. According to one embodiment, this rinse step may be repeated multiple times. In a preferred embodiment, the rinse step is repeated for a total of four times. After the rinse step, the placental globe pieces may be placed in a sterile container (e.g., carboy) containing a sterile saline solution. According to one embodiment, the sterile saline solution comprises from about 0.9% to about 20% NaCl. According to a preferred embodiment, the sterile saline solution is 18%. The container may then be placed on an orbital shaker. In a preferred embodiment, the container is placed on an orbital shaker programmed for 80 revolutions per minute for two hours. According to one aspect, following removal from the orbital shaker, the solution is drained. The placental globe pieces are removed from the container and may be placed in a handheld press or similar equipment, whereby residual blood and solution are pressed (e.g., removed) from the tissue. According to one embodiment, this pressing step may be repeated multiple times. In a preferred embodiment, the pressing step is repeated for a total of three times. Thereafter, the placental globe pieces may be placed in a sterile container containing a sterile saline solution. According to one embodiment, the sterile saline solution comprises from about 0.9% to about 20% NaCl. According to a preferred embodiment, the sterile saline solution is 0.9%. The container may then be placed on an orbital shaker. In a preferred embodiment, the container is placed on an orbital shaker programmed for 80 revolutions per minute for one hour. According to one aspect, following removal from the orbital shaker, the solution is drained. The placental globe pieces are removed from the container and may be placed in a handheld press or similar equipment, whereby residual blood and solution are pressed (e.g., removed) from the tissue. According to one embodiment, this pressing step may be repeated multiple times. In a preferred embodiment, the pressing step is a singular occurrence. Thereafter, the placental globe pieces may be placed in a sterile container containing a sterile saline solution. According to one embodiment, the sterile saline solution comprises from about 0.9% to about 20% NaCl. According to a preferred embodiment, the sterile saline solution is sterile water. The container may then be placed on an orbital shaker. In a preferred embodiment, the container is placed on an orbital shaker programmed for 80 revolutions per minute for 30 minutes. According to one aspect, following removal from the orbital shaker, the solution is drained.

Thereafter, the placental globe pieces may be subjected to morselization. As used herein, "morselization" means to grind up to particle form. Tissue morselization may occur by any art-recognized method of tissue disruption, including, but not limited to: milling, blending, sonicating, homogenizing, micronizing, pulverizing, macerating, or a combination thereof. In one embodiment, the placental globe pieces are subjected to cryogenic milling by methods commonly known in the art. In a preferred embodiment, the tissue is cryogenically milled in a CryoMill® (available from Retsch) for two cycles at a frequency 1/s of 25 Hz with a pre-cooling time of no more than about five minutes, a grinding time of no more than about two minutes, and an intermediate cooling time of no more than about five minutes. In another embodiment, a Freezer/Mill® available from SPEX SamplePrep, LLC may be used. In another embodiment, an IKA® M 20 universal mill may be used. In some embodiments, the placental globe pieces are morselized by use of a tissue grinder (e.g., a Potter-Elvehjem grinder or a Wheaton Overhead Stirrer). In some embodiments, the placental globe pieces are morselized by use of a sonicator. In some embodiments, the placental globe pieces are morselized by use of a bead beater. In some embodiments, the placental globe pieces are morselized by use of a freezer/mill (e.g., a SPEX SamplePrep Freezer/Mill). In some embodiments, the placental globe pieces are morselized by manual use of a pestle and mortar. The placental globe pieces may be optionally lyophilized before or after being subjected to morselization.

The particles of the resulting morselized placental globe composition may be micron or submicron size. The resulting placental globe composition may be wet. The resulting placental globe composition may be a dry powder. In some embodiments, the morselized placental globe composition is suspended in one or more biocompatible solvents to create a paste, emulsion or gel. Examples of biocompatible solvents include, but are not limited to, physiological saline; BSS™, a balanced salt solution containing per ml 0.64% sodium chloride, 0.075% potassium chloride, 0.048% calcium chloride, 0.03% magnesium chloride, 0.39% sodium acetate, and 0.17% sodium citrate dihydrate, as well as sodium hydroxide and/or hydrochloric acid to adjust pH, and water; Ocular Irrigation Solution™; Lactated Ringer's solution; normal saline solution; or normal saline adjusted to pH 7.4 with sodium bicarbonate.

Following morselization, the placental globe composition may be placed in a sterile container (i.e., flask) with an ethanol composition. According to one embodiment, the ethanol composition comprises from about 90% to about 100% ethanol. In a preferred embodiment, the ethanol comprises about 100% ethanol. The container may then be placed on an orbital shaker. In a preferred embodiment, the container is placed on an orbital shaker programmed for 80 revolutions per minute for 30 minutes. According to one aspect, following removal from the orbital shaker, the remaining placental globe composition is subjected to vacuum drying. According to a preferred embodiment, the remaining placental globe composition is placed in a 1 L vacuum flask and allowed to vacuum dry for one hour to form the morselized placental composition.

Assembly of Human Birth Tissue Laminate

The invention further provides a human birth tissue laminate comprising two or more membranes and at least one inner layer of morselized placental composition prepared by the methods described herein. The human birth tissue laminate can comprise two or more membranes oriented in a particular fashion. For example, the laminate can comprise two or more membranes in which only the fetal membrane sides of the membranes are in contact; only the maternal sides of the membranes are in contact; or a combination of both. In one embodiment, the human birth tissue laminate comprise two membranes, wherein the two faces of the laminate expose both a fetal membrane side and a maternal membrane side.

The membranes of the present invention can be laminated by stacking two or more layers of membrane one atop the other with a quantity of morselized placental composition placed between each membrane layer. The membrane layers may be laminated either dry or after rehydration. Alternatively, two or more layers of membrane may be laminated prior to initial drying using, for example, a freeze drying process, or drying under moderate heat with or without vacuum or any lamination method known to those skilled in the art. If heat is applied, preferably, the heat is not so high as to cause breakdown or decomposition of the protein components (e.g., collagen) of human birth tissue material components. Typically, the heat applied is less than about 70° C., preferably less than about 60° C., and, more preferably, is approximately 50° C. Lamination time varies with, for example, the number of membrane layers subjected to lamination, but typically takes 1-2 hours at 50° C. Thus, a method of preparing a human birth tissue laminate using a composition comprising two or more membranes and at least one inner layer of morselized placental composition comprises layering a plurality of said membranes in contact with each other to form a laminate.

The human birth tissue laminate of the present invention may also be laminated using an adhesive applied between the two or more layers of membrane. Such an adhesive is preferably appropriate for medical applications, and can comprise a natural biological adhesive, for example tissue glue or tissue adhesive, fibrin glue, fibrinogen glue, hydrogel tissue glue, chondroitin sulfate aldehyde, synthetic adhesive or any combination thereof.

The human birth tissue laminate of the present invention may also be laminated with a non-biological material (e.g., plastic mesh). In a preferred embodiment, the human birth tissue laminate comprises two membrane layers and two layers of mesh, such that the mesh is the outermost layer of both sides of the human birth tissue laminate. However, any combination of membrane layers and non-biological material may be contemplated by the present invention.

In one embodiment, the human birth tissue laminate comprises at least two membranes of approximately the same size and shape aligned one atop the other so that the shape is substantially maintained. Such a laminate can be trimmed to finalize a particular shape. In another embodiment, the laminate comprises two or more membranes of varying shapes and/or sizes.

Figure 4:
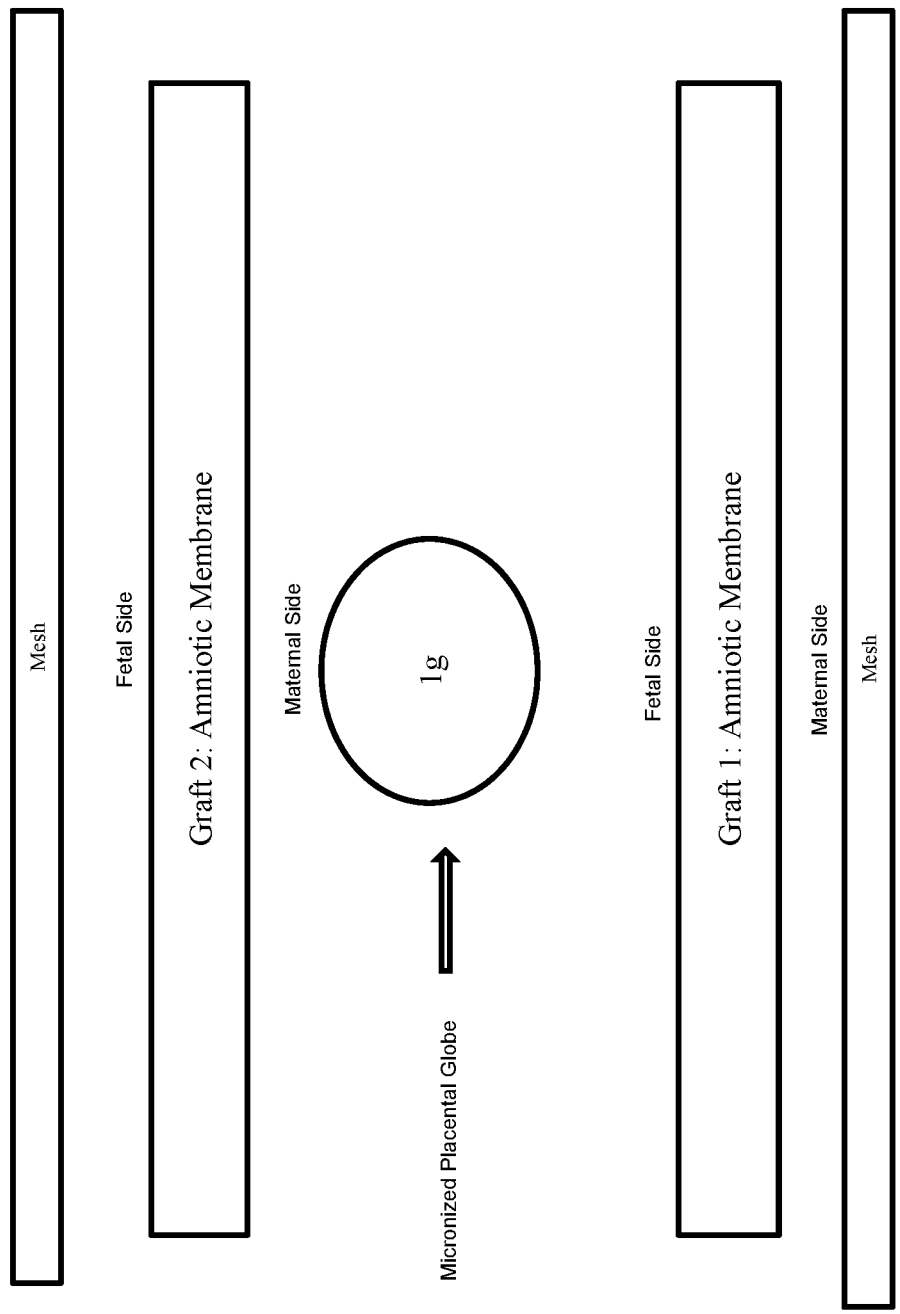
FIG. 4 illustrates a method of preparing a human birth tissue laminate.

As illustrated in FIG. 4, in a preferred embodiment, the substrate (e.g., mesh) is removed from the fetal side of a first membrane prepared by the methods described herein. A quantity of morselized placental composition (e.g., one gram) is placed in the center of the exposed fetal side of the first membrane. Substrate (e.g., mesh) is removed from the maternal side of a second membrane prepared by the methods described herein. Thereafter, the maternal side of the second membrane is placed directly atop (i.e., aligned) the first membrane with centered morselized placental globe composition. In a preferred embodiment, the tri-layer composition is then placed in a vacuum chamber, thereby producing a human birth tissue laminate graft.

In certain embodiments, the human birth tissue laminate is packaged in a dry state. In other embodiments, the human birth tissue laminate is packaged in a wet state, including, but not limited to, sterile water, crystalloids, ethanol, or another sterilizing, preserving or storage agent. The packaged human birth tissue laminate can be terminally sterilized using any method known in the art, including irradiation (e.g., gamma or electron beam irradiation) and supercritical fluid technologies (e.g., supercritical carbon dioxide). In one embodiment, an electron beam irradiation is applied in an amount up to about 45 kGy. The sterilized human birth tissue laminate may be stored for up to typically about two years from the date of processing. In one embodiment, the human birth tissue laminate may be stored under proper conditions for as much as about five years following processing. The sterilized human birth tissue laminate may be stored in any container suitable for long-term storage. Preferably, the sterilized human birth tissue laminate is stored in a sterile double peel-pouch package.

A method of treating a wound is also provided. According to one embodiment, the human birth tissue laminate graft is prepared according to the methods as provided herein. A medical professional can place the human birth tissue laminate graft on or around a wound or defect, including a surgical site. In one embodiment, the wound includes, but is not limited to, at least one diabetic ulcer, decubitus ulcer, venous leg ulcer, arterial leg ulcer, cutaneous ulcer, or a wound arising on or around a soft tissue, nerve, organ, vascular tissue, muscle, spinal cord, bone, oral cavity, ocular surface, or a combination thereof. In one embodiment, the defect is a soft tissue defect or bone void. In another embodiment, the human birth tissue laminate graft may be used, for example, in surgical procedures including, but not limited to, spine surgeries, knee surgeries, shoulder surgeries, OB/GYN procedures, urological procedures, plastic surgeries, trauma-related cases, cardiovascular procedures, brain/neurological procedures, sport injury surgeries, soft tissue repair, burn and wound care, or in any other procedure where a human birth tissue laminate graft is desirable. In one embodiment, the human birth tissue laminate may be used as an adhesion barrier or a bariatric staple strip. In a preferred embodiment, the human birth tissue laminate graft may be used to treat: stress urinary incontinence, pelvic floor reconstruction/augmentation, post-lumpectomy reconstruction/augmentation, limb salvage, muscle regeneration, rotator cuff overlay/augmentation, facial reconstruction/augmentation, amputation "stump" revision, avulsion repair/augmentation, Peyronie's disease repair, tendon tear wrap/augmentation, gum and palate augmentation and deep scar revisions.

In a preferred embodiment, the human birth tissue laminate may be used in guided tissue regeneration techniques, e.g., to regenerate or replace diseased or damaged tissue, including soft tissue and bone. The invention encompasses use of the human birth tissue laminate by directly implanting the laminate at the site of treatment. The human birth tissue laminate is particularly useful in any circumstance, such as following surgery (e.g., dental surgery) where enhanced wound healing and/or replacement of dermis is desirable.

The human birth tissue laminate graft may be adjusted to a desired size and shape at the time of implantation by a medical professional using any method known in the art (e.g., trimming and suturing). In certain embodiments, no sutures are required for the human birth tissue laminate graft to remain in place onto or around a wound, defect or application site. In other embodiments, the human birth tissue laminate graft may be utilized with at least one composition or device for delivering, fastening or fixing the human birth tissue laminate graft on or around a wound, defect, application site or a portion thereof. Exemplary compositions include, but are not limited to, tissue glue or tissue adhesive, fibrin glue, fibrinogen glue, hydrogel tissue glue, chondroitin sulfate aldehyde, or natural proteins. Exemplary devices include, but are not limited to, sutures, staples or forceps. The human birth tissue laminate graft may be hydrated prior to application. In other embodiments, the human birth tissue laminate graft may not be hydrated prior to application.

If desired, the human birth tissue laminate may be treated to provide for the delivery of a variety of antibiotics, anti-inflammatory agents, growth factors and/or other specialized proteins or small molecules that assist in the healing cascade after placement.

A kit for use by a medical transplant professional is also provided. According to one embodiment, the kit includes one or more packaged and sterilized human birth tissue laminates as provided herein and at least one set of instructions. The kit may further include at least one composition or device for delivering, fastening or fixing the human birth tissue laminate in place onto or around a wound. The kit may further include a container adapted to accommodate the aforementioned components while preserving the human birth tissue laminate as per applicable Food and Drug Administration guidelines.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

Having generally described the present invention, a further understanding can be obtained by reference to the examples provided herein for purposes of illustration only and are not intended to be limiting.

EXAMPLE 1

The human birth tissue laminate was prepared according to the methods described herein. Human birth tissue was obtained from a seronegative healthy female via Cesarean section. To maximize the overall quality of the donated tissue, a recovery technician was present in the operating room during the donor's Cesarean section to assist the physician with recovery, treatment and handling of the birth tissue. The donor was surgically prepped and draped per AORN standards prior to the Cesarean section procedure. The recovery technician prepared the recovery site by establishing a sterile field on a back table in the operating room. Following delivery of the baby, the physician's assistant placed the human birth tissue en-bloc into a sterile basin. Maintaining sterility, the basin was transferred to the recovery technician onto the sterile field. Beginning at the amnion/chorion membrane surgical incision site, the recovery technician used blunt dissection to separate the chorionic membrane from the amniotic membrane, using care not to tear the amniotic tissue. The recovery technician then removed the amniotic membrane from the placental globe until reaching the umbilical cord. At the site where the amnion is attached to the umbilical cord, the recovery technician dissected the amnion from the umbilical cord by making an incision in the amnion around the circumference of the umbilical cord. The amniotic membrane was transferred to a sterile container and rinsed with 18% NaCl to remove any blood or debris. This rinse step was repeated two more times, for a total of three rinse steps following recovery of the amniotic membrane.

After thorough rinsing, the amniotic membrane was transferred into a sterile bag. Approximately 300 ml of transport solution (18% NaCl) was added to the sterile bag containing the recovered amniotic membrane. The bag was secured with a knot. The single-bagged amniotic membrane was then placed into a second sterile bag, which was securely knotted. The double-bagged amniotic membrane was then transferred into a plastic transport container to which the appropriate identification was affixed.

The remaining birth tissue material, including the placental globe (with attached chorion) and the umbilical cord, was transferred to a sterile container and rinsed with 18% NaCl to remove any blood or debris. This rinse step was repeated two more times, for a total of three rinse steps following recovery of the birth tissue material.

After thorough rinsing, the birth tissue material, including the placental globe (with attached chorion) and the umbilical cord were transferred into a sterile bag. Approximately 500 ml of transport solution (18% NaCl) was added to the sterile bag containing the birth tissue material. The bag was secured with a knot. The single-bagged birth tissue material was then placed into a second sterile bag, which was securely knotted. The double-bagged birth tissue material was then transferred into a plastic transport container to which the appropriate identification was affixed.

The plastic transport container was placed in a qualified shipping container with an appropriate amount of wet ice to maintain refrigerated temperatures. The validated box arrived at the processing facility approximately 30 minutes following recovery and was immediately placed in refrigerated temperatures (1-10° C.) and inspected per standard operating procedures.

All processing steps were performed on a sterile field using aseptic technique in a validated cleanroom at the processing facility. All manufacturing steps were recorded concurrently by a circulating technician on a designated processing record.

The birth tissue material, including the placental globe (with attached chorion) and the umbilical cord, was removed from the plastic transport container and outer bag. The inner bag containing the birth tissue material was aseptically passed onto a sterile field. A sterile technician incised the umbilical cord from the placental globe, discarding the umbilical cord. A sterile technician removed the chorion from the placental globe utilizing blunt dissection, discarding the chorion after removal.

The placental globe was processed according to the steps provided herein. The placental globe was cut into small pieces (non-uniform) using mayo scissors. The placental globe pieces were placed in a handheld press, whereby residual blood and solution were pressed from the tissue. Immediately following the press step, the placental globe pieces were rinsed with 18% NaCl. A sterile technician pressed and rinsed the placental globe pieces for a total of four times. Immediately thereafter, the placental globe pieces were placed in a sterile 9 L carboy containing 18% NaCl. The carboy was placed on an orbital shaker (set for 80 revolutions per minute) for two hours. At the end of the second hour, the 9 L carboy was removed from the orbital shaker and the solution was drained. The remaining placental globe pieces were pressed through the handheld press three times. Immediately thereafter, the placental globe pieces were placed in a sterile carboy containing 3 L of 0.9% NaCl and allowed to agitate on the orbital shaker (80 revolutions per minute) for one hour. At the end of the one hour, the carboy was removed from the orbital shaker and the solution was drained. The remaining placental globe pieces were pressed through the handheld press one time. Then, the placental globe pieces were placed in a sterile carboy containing sterile water and allowed to agitate on the orbital shaker (80 revolutions per minute) for 30 minutes. At the end of the 30 minutes, the carboy was removed from the orbital shaker and the solution was drained.

Thereafter, the placental globe pieces were milled using an IKA® M 20 universal mill and then placed in a 2 L sterile flask with 1 L of 100% ethanol. The flask was placed on the orbital shaker (set to 80 revolutions per minute) and allowed to agitate for 30 minutes. The remaining composition was then placed into a 1 L vacuum flask and allowed to vacuum dry for one hour to form the milled placental globe composition.

Simultaneous with the aforementioned one hour vacuum drying step, the amniotic membrane was removed from the plastic transport container and outer bag. The inner bag containing the amniotic membrane was aseptically passed onto a sterile field. The amniotic membrane was placed maternal side up onto a sterile cutting board. The membrane was inspected for any damage or debris. Any stringy ends were cut away. Keeping the membrane flat on the sterile cutting board, the amnion was rinsed with a sterile saline solution (0.9% NaCl). The maternal side of the membrane was covered with sterile mesh, allowing the mesh to slightly overlap the membrane. The membrane was gently lifted, positioned fetal side up, and placed back on the sterile cutting board, using caution to not disturb the mesh/amnion interface. The fetal side of the membrane was rinsed with a sterile saline solution (0.9% NaCl). Then, the fetal side of the membrane was covered with sterile mesh, allowing the mesh to slightly overlap the membrane. Using a rotary cutting blade, the amniotic membrane was sectioned into 4 cm×4 cm amnion squares.

The 4 cm×4 cm amnion squares and the milled placental globe composition were placed on a sterile field. Human birth tissue laminate grafts were assembled as described herein. Mesh was removed from the fetal side of a first amnion square. One gram of milled placental globe composition was placed in the center of the exposed fetal side of the first amnion square. Mesh was removed from the maternal side of a second amnion square. The maternal side of the second amnion square was placed atop the first amnion square with centered milled placental globe composition. This process was repeated 25 times, thereby creating 25 tri-layer tissue grafts as illustrated in the embodiment of FIG. 4. Thereafter, the grafts were placed in a vacuum chamber. Upon completion of the drying cycle, the grafts were removed from the vacuum chamber, resulting in 25 human birth tissue laminate grafts.

Each human birth tissue laminate graft was packaged in a sterile foil inner pouch using aseptic technique. Using an AccuSeal 540Plus sealer, each foil pouch was sealed inside a Tyvek pouch following standard operating procedures. Each Tyvek pouch was assigned and labeled with a tissue identification number, designed to ensure the traceability of tissue from receipt through clinical use, transfer or destruction. Each unit was terminally sterilized via E Beam irradiation.

I claim:

1. A human birth tissue laminate graft comprising:
   a first amniotic membrane;
   a second amniotic membrane; and
   a pre-determined amount of a morselized placental composition, the morselized placental composition located between a fetal side of the first amniotic membrane and maternal side of the second amniotic membrane thereby forming a human birth tissue laminate,
   wherein the morselized placental composition includes at least one human birth tissue material selected from the group consisting of placental globe, umbilical cord, umbilical cord blood, umbilical cord vessel(s), amniotic fluid, and any combination thereof,
   wherein at least one of the first and second amniotic membranes is chemically dehydrated, and
   wherein the human birth tissue laminate graft is terminally sterilized using gamma irradiation or electron beam irradiation.

2. The human birth tissue laminate graft of claim 1, wherein the first amniotic membrane, second amniotic membrane or both the first amniotic membrane and second amniotic membrane are cross-linked.

3. The human birth tissue laminate graft of claim 1, further comprising an adhesive on either or both of the first or second amniotic membrane.

4. The human birth tissue laminate graft of claim 1, wherein the human birth tissue laminate is packaged in a dry state.

5. The human birth tissue laminate graft of claim 1, wherein the human birth tissue laminate is packaged in a wet state.

6. The human birth tissue laminate graft of claim 1, further comprising a mesh on the maternal side of the first amniotic membrane and a mesh on the fetal side of the second amniotic membrane.

7. The human birth tissue laminate graft of claim 1, wherein the human birth tissue laminate is fully resorbable by the body.

8. The human birth tissue laminate graft of claim 1, wherein the first amniotic membrane and second amniotic membrane are of the same size and shape.

9. The human birth tissue laminate graft of claim 1, wherein the second amniotic membrane is placed over the morselized placental composition such that the first and second amniotic membranes are aligned.

10. A kit for use by a medical professional, comprising:
    one or more packaged human birth tissue laminates according to claim 1; and at least one set of instructions.

11. The kit of claim 10, wherein the packaged human birth tissue laminate graft is terminally sterilized using gamma irradiation or electron beam irradiation.

12. A method of treating a wound or defect comprising the step of: placing the human birth tissue laminate graft of claim 1 on or around the wound or defect.

13. The method of claim 12, wherein the wound includes a diabetic ulcer, decubitus ulcer, venous leg ulcer, arterial leg ulcer, cutaneous ulcer, or a wound arising on or around a soft tissue, nerve, organ, vascular tissue, muscle, spinal cord, bone, oral cavity, ocular surface, or a combination thereof.

14. The method of claim 12, wherein the defect is a soft tissue defect or bone void.

15. The method of claim 12, further comprising the step of hydrating the human birth tissue laminate graft prior to placement.

16. A method of promoting regeneration of diseased or damaged tissue comprising the steps of:

placing the human birth tissue laminate graft of claim 1 on or around the diseased or damaged tissue.

17. The method of claim 16, wherein the diseased or damaged tissue is a nerve, organ, vascular tissue, muscle, spinal cord, bone, oral cavity, ocular surface, or a combination thereof.

18. The method of claim 16, further comprising the step of hydrating the human birth tissue laminate graft prior to placement.

* * * * *